United States Patent [19]
Hoffmann et al.

[11] 3,949,022
[45] Apr. 6, 1976

[54] N-[N',N'-DISUBSTITUTED-AMINOMETHYLIDENE]-(THIONO)THIOL-PHOSPHORIC ACID ESTER IMIDES

[75] Inventors: Hellmut Hoffmann, Wuppertal; Ingeborg Hammann, Cologne; Günter Unterstenhöfer, Opladen, all of Germany

[73] Assignee: Bayer Aktiengesellschaft, Leverkusen, Germany

[22] Filed: Jan. 21, 1974

[21] Appl. No.: 435,055

Related U.S. Application Data
[62] Division of Ser. No. 345,399, March 27, 1973.

[30] Foreign Application Priority Data
Apr. 6, 1972  Germany............................ 2216552

[52] U.S. Cl...... 260/943; 260/247.1 R; 260/293.85; 260/326.61; 260/945; 260/968; 424/200; 424/203; 424/211
[51] Int. Cl.²...................... C07F 9/24; A01N 9/36
[58] Field of Search..................... 260/943, 944, 945

[56] References Cited
UNITED STATES PATENTS
3,801,679   4/1974   Hoffman (n) et al. ............. 260/945

*Primary Examiner*—Anton H. Sutto
*Attorney, Agent, or Firm*—Burgess, Dinklage & Sprung

[57] ABSTRACT

N-[N',N'-disubstituted-aminomethylidene]-(thiono)thiolphosphoric acid ester imides of the formula

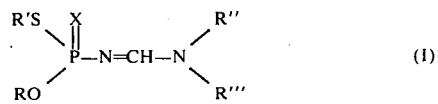

in which
R is alkyl with 1 to 6 carbon atoms,
R' is alkyl, alkenyl or alkynyl with up to 6 carbon atoms, lower alkylmercapto-lower alkyl or N-alkyl-carbamoylmethyl,
R'' and R''' each independently is alkyl or alkenyl with up to 6 carbon atoms, or conjointly with the nitrogen atom form a heterocyclic ring, and X is oxygen or sulfur,
which possess insecticidal, acaricidal and nematocidal properties.

4 Claims, No Drawings

N-[N',N'-DISUBSTITUTED-AMINOMETHYLIDENE]-(THIONO)THIOL-PHOSPHORIC ACID ESTER IMIDES

This is a division of application Ser. No. 345,399 filed Mar. 27, 1973.

The present invention relates to and has for its objects the provision of particular new N-[N',N'-disubstituted-aminomethylidene]-(thiono)thiol-phosphoric acid ester imides which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, especially insects and acarids, with other and further objects becoming apparent from a study of the within specification and accompanying examples.

It is already known from German DOS No. 2,014,027 that O,S-dialkyl-N-acetyl-thiolphosphoric acid ester amides, for example O-methyl- (Compound A) or O-ethyl-S-methyl-N-acetyl-thiolphosphoric acid ester amide (Compound B), possess insecticidal and acaricidal properties.

The present invention provides N-[N',N'-disubstituted-aminomethylidene] —(thiono)thiol-phosphoric acid ester imides of the general formula

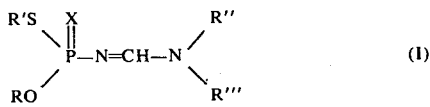  (I)

in which
  R is alkyl with 1 to 6 carbon atoms,
  R' is alkyl, alkenyl or alkynyl with up to 6 carbon atoms, lower alkylmercapto-lower alkyl, or N-alkyl-carbamoylmethyl,
  R" and R''' each independently is alkyl or alkenyl with up to 6 carbon atoms, or conjointly with the nitrogen atom form a heterocyclic ring, and
  X is oxygen or sulfur.

Preferably, R is lower alkyl with 1 to 4 carbon atoms, R' is lower alkyl, alkenyl or alkynyl with up to 4 carbon atoms, N-monomethylcarbamoylmethyl, N-monoethyl-carbamoylmethyl, methylmercaptoethyl or ethylmercaptoethyl, and R" and R''' are alkyl or alkenyl with up to 4 carbon atoms or conjointly with the nitrogen atom form a 5-membered or 6-membered heterocyclic ring which is optionally interrupted by a nitrogen atom, a sulfur atom or especially an oxygen atom.

Surprisingly, the disubstituted N-[aminomethylidene]-thiol(thiono)-phosphoric acid ester imides according to the invention possess a substantially better insecticidal (especially systemic-insecticidal) and acaricidal action than the previously known O,S-dialkyl-N-acetyl-thiolphosphoric acid ester amides of analogous structure and similar type of action. The compounds according to the invention thus represent a genuine enrichment of the art. Furthermore, the new compounds contribute to meeting the great need for active compounds in the field of pesticides. The latter arises from the fact that the commercially available agents have to meet constantly higher standards, particularly in respect of the protection of the environment, such as low toxicity to warm-blooded animals and phytotoxicity, rapid degradation in and on the plant with short minimum intervals to be observed between spraying with pesticide and harvesting, and activity against resistant pests.

The present invention also provides a process for the production of a disubstituted N-[aminomethylidene]-thiol-(thiono)-phosphoric acid ester imide of the formula (I) in which:
  a. a phosphorylated iminoformic acid alkyl ester of the general formula

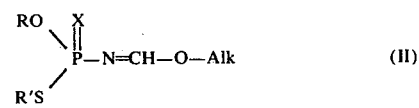  (II)

is reacted with a secondary amine of the general formula

  (III)

or
  b. a (thiono)thiol-phosphoric acid ester amide of the general formula

  (IV)

is reacted with a formamide-acetal of the general formula

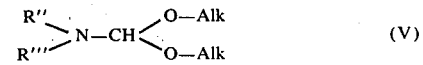  (V)

in which formulae (II) to (V) R, R', R", R''' and X have the above-mentioned meanings and
  Alk is an alkyl radical with 1 to 6 carbon atoms.

If N-(O,S-dimethylthiolphosphoryl)-iminoformic acid ethyl ester and diethylamine or O,S-diethylthiolphosphoric acid ester amide and N,N-diethylformamide-dimethylacetal are used as the starting compounds, the course of the reaction of the two process variants can be represented by the following formula schemes:

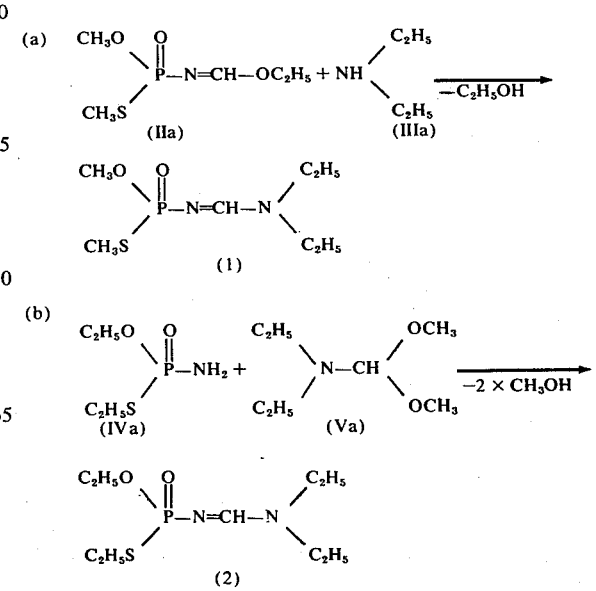

The amines (III) required as starting compounds are known and can be readily prepared on an industrial scale, while the acetals (V) are in some cases still new but can be prepared according to processes which are known in principle as described in Ber. 101 (1968), page 46.

The following may be mentioned as examples of amines and acetals to be employed in accordance with the process: diethylamine, di-n-propylamine, di-isopropylamine, di-n-butylamine, di-isobutylamine, di-sec.-butylamine, di-tert.-butylamine, di-n-pentylamine, di-n-hexylamine, diallylamine, pyrrolidine, piperidine and morpholine, and N,N-(diethyl-, di-n-propyl-, di-iso-propyl-, di-n-butyl-, di-iso-butyl-, di-tert.-butyl-, di-sec.-butyl, dipentyl-, diallyl)-formamide-dimethyl- and -diethyl-acetal, and also the acetals of 1-pyrrolidinaldehyde, morpholinaldehyde and piperidinaldehyde.

The thiol(thiono)-phosphoric acid ester amides (IV) required as starting compounds are mostly described in the literature. The compounds which are still new can be prepared in a manner which is in principle known as described in German DOS Nos. 1,221,633 and 1,077,215, U.S. Pat. No. 3,309,266 and French Patent Specification 1,508,632. The following may be mentioned as examples: S-methyl-, S-ethyl, S-n-propyl, S-iso-propyl-, S-n-butyl-, S-iso-butyl, S-sec.-butyl-, S-tert.-butyl, S-allyl-, S-butenyl-, S-propynyl-, S-butynyl-, S-(N-monomethylcarbamoylmethyl)-, S-(N-monoethylcarbamoylmethyl)-, S-methylmercaptoethyl-, S-ethylmercaptoethyl-O-methyl- or-O-ethyl-, -O-n-propyl-, -O-iso-propyl-, -O-n-butyl-, -O-sec.-butyl-, -O-tert.-butyl- and -O-iso-butylthiolophosphoric acid ester amide and the corresponding thiono analogues.

The phosphorylated iminoformic acid alkyl esters (II) required as starting compounds are new; they can be prepared according to a new process from the (thiono)thiol-phosphoric diester amides known from the literature, e.g. German DOS Nos. 1,221,633 and 1,077,215, U.S. Pat. No. 3,309,266 and orthoformic acid alkyl esters. The following may be mentioned as examples: N-[S-methyl- or S-ethyl-, S-n-propyl-, S-iso-propyl-, S-n-butyl-, S-iso-butyl-, S-sec.-butyl-, S-tert.-butyl-, S-methylmercaptoethyl-, S-ethylmercaptoethyl-, S-(N'-monomethylcarbamoylmethyl)-, S-(N'-monoethylcarbamoylmethyl)-, S-allyl-, S-propenyl-, S-propynyl- and S-butenyl-O-methylthiolophosphoryl]-iminoformic acid methyl ester and ethyl ester, the corresponding O-ethyl, O-propyl and O-butyl derivatives and their thiono analogues.

Both process variants (a) and (b) can be carried out with the use of a solvent or diluent. As such, practically all inert organic solvents can be used. These include above all aliphatic and aromatic hydrocarbons such as benzene, toluene, xylene and benzine, and also alcohols, such as ethanol and n-butanol, as well as nitriles, such as acetonitrile and propionitrile.

The reaction temperature can be varied within a wide range. In general, temperatures from 0° to 150°C are used, preferably about 40° to 60°C in the case of process variant (a) and about 100° to 130°C in the case of process variant (b). The reaction is generally carried out under normal pressure.

To carry out process variant (a), the reactants are generally employed in an equimolar ratio, mostly without solvents, and the mixture may be stirred for from one to several hours at the indicated temperatures; thereafter the reaction solution may be subjected to "slight distillation".

In process variant (b), the acetal component is in most cases employed in 20 to 30% molar excess and the reaction mixture — generally without solvents — may be heated for several hours at the indicated temperatures. Here again the mixture may be worked up in the usual manner by "slight distillation".

The compounds according to the invention are generally obtained in the form of oils which cannot be distilled without decomposition; they may therefore be freed from any remaining volatile constituents by so-called slight distillation, that is to say by prolonged heating under reduced pressure to moderately elevated temperatures, and they can be purified in this way. They are characterized by the refractive index.

As has already been mentioned, the new disubstituted N-[aminomethylidene]-thiolo(thiono)-phosphoric acid ester imides are distinguished by an outstanding insecticidal, especially systemic-insecticidal, and acaricidal activity against plant pests, hygiene pests and pests of stored products. They possess a good action both against sucking and against biting insects and mites (Acarina). While possessing a low phytotoxicity, some of them additionally also display a soil-insecticidal and/or nematocidal action.

For this reason, the compounds according to the invention may be successfully employed as pesticides, especially in plant protection.

To the sucking insects there belong, in the main, aphids (Aphidae) such as the green peach aphid (Myzus persicae), the bean aphid (Doralis fabae), the bird cherry aphid (Rhopalosiphum padi), the pea aphid (Macrosiphum pisi) and the potato aphid (Macrosiphum solanifolii), the currant gall aphid (Cryptomyzus korschelti), the rosy apple aphid (Sappaphis mali), the mealy plum aphid (Hyalopterus arundinis) and the cherry blackfly (Myzus cerasi); in addition scales and mealybugs (Coccina), for example the oleander scale (Aspidiotus hederae) and the soft scale (Lecanium hesperidum) as well as the grape mealybug (Pseudococcus maritimus); thrips (Thysanoptera), such as Hercinothrips femoralis, and bugs, for example the beet bug (Piesma quadrata), the red cotton bug (Dysdercus intermedius), the bed bug (Cimex lectularius), the assassin bug (Rhodnius prolixus) and Chagas' bug (Triatoma infestans) and, further, cicadas, such as Euscelis bilobatus and Nephotettix bipunctatus.

In the case of the biting insects, above all there should be mentioned butterfly caterpillars (Lepidoptera) such as the diamond-back moth (Plutella maculipennis), the gypsy moth (Lymantria dispar), the brown-tail moth (Euproctis chrysorrhoea) and tent caterpillar (Malacosoma neustria); further, the cabbage moth (Mamestra brassicae) and the cutworm (Agrotis segetum), the large white butterfly (Pieris brassicae), the small winter moth (Cheimatobia brumata), the green oak tortrix moth (Tortrix viridana), the fall armyworm (Laphygma frugiperda) and cotton worm (Prodenia litura), the ermine moth (Hyponomeuta padella), the Mediterranean flour moth (Ephestia kuehniella) and greater wax moth (Galleria mellonella).

Also to be classed with the biting insects are beetles (Coleoptera), for example the granary weevil (Sitophilus granarius = Calandra granaria), the Colorado beetle (Leptinotarsa decemlineata), the dock beetle (Gastrophysa viridula), the mustard beetle (Phaedon cochleariae), the blossom beetle (Meligethes aeneus), the raspberry beetle (Byturus tomentosus), the bean weevil (Bruchidius = Acanthoscelides obtectus), the leather beetle (Dermestes frischi), the khapra beetle (Trogoderma granarium), the flour beetle (Tribolium

*castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Acheta domesticus*); termites such as the eastern subterranean termite (*Reticulitermes flavipes*) and Hymenoptera such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acari*) there are classed, in particular, the spider mites (*Tetranychidae*) such as the two-spotted spider mite (*Tetranychus telarius = Tetranychus althaeae* or *Tetranychus urticae*) and the European red mite (*Paratetranychus pilosus = Panonychus ulmi*), gall mites, for example the black-currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or rodenticides, fungicides, bactericides, herbicides, fertilizers, growth-regulating agents, etc., if desired, or in the form of particular dosage preparations for specific application made therefrom, such as solutions, amulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplates those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably incuding a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, a correspondingly combative or toxic amount, i.e. an insecticidally, acaricidally or nematodically effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrustation, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the indicated amount of solvent, which contained the indicated amount of emulsifier, and the concentrate was diluted with water to the desired concentration.

Cabbage leaves (*Brassica oleracea*) were sprayed with the preparation of the active compound until dripping wet and were then infested with mustard beetles larvae (*Phaedon cochleariae*).

After the indicated periods of time, the degree of destruction was determined in %. Here, 100% means that all beetle larvae were killed. 0% means that no beetle larvae were killed.

The active compounds, the concentration of the active compounds, the times of evaluation and the results can be seen from the following Table 1:

Table 1
(*Phaedon* larvae test)

| Active compound | Active compound concentration in % by weight | Degree of destruction in % after 3 days |
| --- | --- | --- |
| 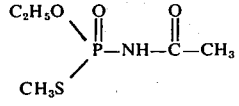 (known) (B) | 0.1<br>0.01 | 90<br>0 |
| 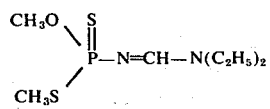 (11) | 0.1<br>0.01 | 100<br>60 |
| 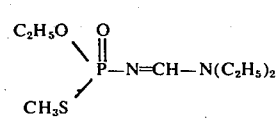 (21) | 0.1<br>0.01 | 100<br>100 |
| 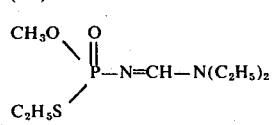 (10) | 0.1<br>0.01 | 100<br>100 |
| 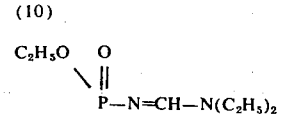 (2) | 0.1<br>0.01 | 100<br>70 |

Table 1-continued
(*Phaedon* larvae test)
| Active compound | Active compound concentration in % by weight | Degree of destruction in % after 3 days |
|---|---|---|
| 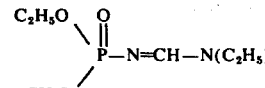 (4) | 0.1<br>0.01 | 100<br>100 |
| 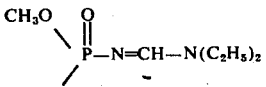 (8) | 0.1<br>0.01 | 100<br>90 |
| 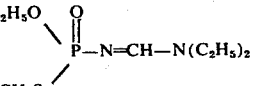 (9) | 0.1<br>0.01 | 100<br>90 |
| 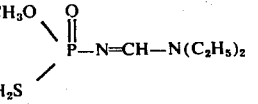 (3) | 0.1<br>0.01<br>0.001 | 100<br>100<br>50 |
| 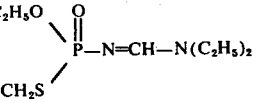 (7) | 0.1<br>0.01 | 100<br>100 |
| 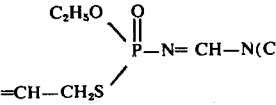 (6) | 0.1<br>0.01 | 100<br>100 |
| 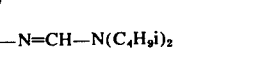 (18) | 0.1<br>0.01 | 100<br>60 |
| 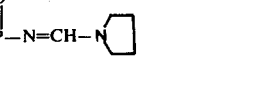 (20) | 0.1<br>0.01 | 100<br>85 |
| 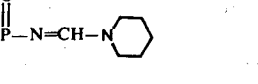 (14) | 0.1<br>0.01 | 100<br>65 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphide (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 2:

Table 2 (*Myzus* test)

| Active compound | Active compound concentration in % by weight | Degree of destruction in % after 1 day |
|---|---|---|
| $\begin{array}{c}C_2H_5O\\ \phantom{xx}\diagdown\\ \phantom{xxx}P-NH-\underset{\underset{O}{\parallel}}{C}-CH_3\\ \phantom{xx}\diagup\\ CH_3S\end{array}$ (known) (B) | 0.01<br>0.001 | 20<br>0 |
| $\begin{array}{c}CH_3O\\ \phantom{xx}\diagdown\overset{S}{\parallel}\\ \phantom{xxx}P-N=CH-N(C_2H_5)_2\\ \phantom{xx}\diagup\\ CH_3S\end{array}$ (11) | 0.01<br>0.001 | 100<br>85 |
| $\begin{array}{c}CH_3O\\ \phantom{xx}\diagdown\overset{O}{\parallel}\\ \phantom{xxx}P-N=CH-N(C_2H_5)_2\\ \phantom{xx}\diagup\\ CH_3S\end{array}$ (1) | 0.01<br>0.001<br>0.0001 | 100<br>95<br>50 |
| $\begin{array}{c}CH_3O\\ \phantom{xx}\diagdown\overset{O}{\parallel}\\ \phantom{xxx}P-N=CH-N(C_2H_5)_2\\ \phantom{xx}\diagup\\ C_2H_5S\end{array}$ (10) | 0.01<br>0.001 | 100<br>100 |
| $\begin{array}{c}C_2H_5O\\ \phantom{xx}\diagdown\overset{O}{\parallel}\\ \phantom{xxx}P-N=CH-N(C_2H_5)_2\\ \phantom{xx}\diagup\\ C_2H_5S-CH_2-CH_2S\end{array}$ (4) | 0.01<br>0.001 | 100<br>50 |
| $\begin{array}{c}CH_3O\\ \phantom{xx}\diagdown\overset{O}{\parallel}\\ \phantom{xxx}P-N=CH-N(C_2H_5)_2\\ \phantom{xx}\diagup\\ CH_2=CH-CH_2S\end{array}$ (8) | 0.01<br>0.001 | 100<br>80 |
| $\begin{array}{c}C_2H_5O\\ \phantom{xx}\diagdown\overset{O}{\parallel}\\ \phantom{xxx}P-N=CH-N(C_2H_5)_2\\ \phantom{xx}\diagup\\ CH_2=CH-CH_2S\end{array}$ (9) | 0.01<br>0.001 | 99<br>50 |
| $\begin{array}{c}CH_3O\\ \phantom{xx}\diagdown\overset{O}{\parallel}\\ \phantom{xxx}P-N=CH-N(C_2H_5)_2\\ \phantom{xx}\diagup\\ CH\equiv C-CH_2S\end{array}$ (3) | 0.01<br>0.001<br>0.0001 | 100<br>100<br>40 |
| $\begin{array}{c}C_2H_5O\\ \phantom{xx}\diagdown\overset{O}{\parallel}\\ \phantom{xxx}P-N=CH-N(C_2H_5)_2\\ \phantom{xx}\diagup\\ CH\equiv C-CH_2S\end{array}$ (7) | 0.01<br>0.001 | 100<br>70 |

Table 2-continued

| Active compound | (*Myzus* test) Active compound concentration in % by weight | Degree of destruction in % after 1 day |
|---|---|---|
| ![compound 6] C₂H₅O\P(=O)(−N=CH−N(C₂H₅)₂)/CH₃−CH=CH−CH₂S (6) | 0.01<br>0.001 | 100<br>30 |
| ![compound 5] C₂H₅O\P(=O)(−N=CH−N(C₂H₅)₂)/CH₃−NH−CO−CH₂S (5) | 0.01<br>0.001 | 100<br>70 |
| ![compound 13] CH₃O\P(=O)(−N=CH−N(CH₂−CH=CH₂)₂)/CH₃S (13) | 0.01 | 100 |
| ![compound 19] CH₃O\P(=O)(−N=CH−N⟨piperidine⟩)/CH₃S (19) | 0.01<br>0.001 | 100<br>50 |

EXAMPLE 3

Doralis test (systemic action)

Solvent: 3 parts by weight of acetone
Emulsifier: 1 part by weight of alkylaryl polyglycol ether To produce a suitable preparation of active compound, 1 part by weight of the active compound was mixed with the indicated amount of solvent which contained the indicated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation of the active compound penetrated into the soil without wetting the leaves of the bean plants. The active compound was absorbed from the soil by the bean plants and thus reached the infested leaves.

After the indicated periods of time, the degree of destruction was determined in %. Here, 100% means that all aphids were killed and 0% means that no aphids were killed.

The active compounds, the concentration of the active compounds, the evaluation times and the results can be seen from the following Table 3:

Table 3

| Active compound | (*Doralis* test/systemic action) Active compound concentration in % by weight | Degree of destruction in % after 4 days |
|---|---|---|
| CH₃O\P(=O)(−NH−C(=O)−CH₃)/CH₃S (known) (A) | 0.01<br>0.001 | 100<br>0 |
| CH₃O\P(=O)(−N=CH−N(C₂H₅)₂)/CH₃S (1) | 0.01<br>0.001<br>0.0001<br>0.00001<br>0.000001 | 100<br>100<br>100<br>100<br>100 |
| C₂H₅O\P(=O)(−N=CH−N(C₂H₅)₂)/CH₃S (21) | 0.01<br>0.001<br>0.0001 | 100<br>100<br>55 |

Table 3-continued

| Active compound | (Doralis test/systemic action) Active compound concentration in % by weight | Degree of destruction in % after 4 days |
| --- | --- | --- |
| $C_2H_5O\diagdown\underset{C_2H_5S-CH_2-CH_2S\diagup}{\overset{O}{\underset{\|\|}{P}}}-N=CH-N(C_2H_5)_2$ <br> (4) | 0.01 <br> 0.001 | 100 <br> 100 |
| $C_2H_5O\diagdown\underset{CH_3-NH-CO-CH_2S\diagup}{\overset{O}{\underset{\|\|}{P}}}-N=CH-N(C_2H_5)_2$ <br> (5) | 0.01 <br> 0.001 <br> 0.0001 | 100 <br> 100 <br> 98 |
| $CH_3O\diagdown\underset{CH_3S\diagup}{\overset{O}{\underset{\|\|}{P}}}-N=CH-N\!\!\bigcirc$ <br> (19) | 0.01 <br> 0.001 <br> 0.0001 | 100 <br> 100 <br> 100 |
| $CH_3O\diagdown\underset{CH_3S\diagup}{\overset{S}{\underset{\|\|}{P}}}-N=CH-N\!\!\bigcirc\!\!O$ <br> (15) | 0.01 <br> 0.001 | 100 <br> 100 |
| $CH_3O\diagdown\underset{CH_3S\diagup}{\overset{O}{\underset{\|\|}{P}}}-N=CH-N\!\!\bigcirc\!\!O$ <br> (16) | 0.01 <br> 0.001 <br> 0.0001 | 100 <br> 100 <br> 90 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the indicated amount of solvent, containing the indicated amount of emulsifier, and the concentrate was diluted with water to the desired concentration.

Bean plants (*Phaseolus vulgaris*) which had a height of about 10–30 cm, were sprayed with the preparation of the active compound until dripping wet. These bean plants were heavily infested with all stages of development of the two-spotted spider mite (*Tetranychus urticae*).

After the indicated periods of time, the effectiveness of the preparation of active compound was determined by counting the dead mites. The degree of destruction thus obtained was expressed in %. 100% means that all spider mites were killed and 0% means that no spider mites were killed.

The active compounds, the concentration of the active compounds, the evaluation times and the results can be seen from the following Table 4:

Table 4

| Active compound | (Tetranychus test/resistant) Active compound concentration in % by weight | Degree of destruction in % after 2 days |
| --- | --- | --- |
| $CH_3O\diagdown\underset{CH_3S\diagup}{\overset{O}{\underset{\|\|}{P}}}-NH-\overset{O}{\underset{\|\|}{C}}-CH_3$ <br> (known)   (A) | 0.1 | 0 |

Table 4-continued
(*Tetranychus* test/resistant)

| Active compound | Active compound concentration in % by weight | Degree of destruction in % after 2 days |
|---|---|---|
| $\begin{array}{c}C_2H_5O\\ \phantom{xx}\diagdown\phantom{x}\underset{\|}{\overset{O}{P}}-NH-\underset{\|}{\overset{O}{C}}-CH_3\\ CH_3S\phantom{xx}\diagup\end{array}$ (known) (B) | 0.1 | 20 |
| $\begin{array}{c}CH_3O\\ \phantom{xx}\diagdown\phantom{x}\underset{\|}{\overset{S}{P}}-N=CH-N(C_2H_5)_2\\ CH_3S\phantom{xx}\diagup\end{array}$ (11) | 0.1 | 99 |
| $\begin{array}{c}CH_3O\\ \phantom{xx}\diagdown\phantom{x}\underset{\|}{\overset{O}{P}}-N=CH-N(C_2H_5)_2\\ CH_3S\phantom{xx}\diagup\end{array}$ (1) | 0.1 | 100 |
| $\begin{array}{c}C_2H_5O\\ \phantom{xx}\diagdown\phantom{x}\underset{\|}{\overset{O}{P}}-N=CH-N(C_2H_5)_2\\ CH_3S\phantom{xx}\diagup\end{array}$ (21) | 0.1 | 100 |
| $\begin{array}{c}CH_3O\\ \phantom{xx}\diagdown\phantom{x}\underset{\|}{\overset{O}{P}}-N=CH-N(C_2H_5)_2\\ C_2H_5S\phantom{xx}\diagup\end{array}$ (10) | 0.1<br>0.01 | 100<br>50 |
| $\begin{array}{c}C_2H_5O\\ \phantom{xx}\diagdown\phantom{x}\underset{\|}{\overset{O}{P}}-N=CH-N(C_2H_5)_2\\ C_2H_5S\phantom{xx}\diagup\end{array}$ (2) | 0.1 | 100 |
| $\begin{array}{c}CH_3O\\ \phantom{xx}\diagdown\phantom{x}\underset{\|}{\overset{O}{P}}-N=CH-N(C_2H_5)_2\\ CH_2=CH-CH_2S\phantom{xx}\diagup\end{array}$ (8) | 0.1<br>0.01 | 95<br>80 |
| $\begin{array}{c}C_2H_5O\\ \phantom{xx}\diagdown\phantom{x}\underset{\|}{\overset{O}{P}}-N=CH-N(C_2H_5)_2\\ CH_2=CH-CH_2S\phantom{xx}\diagup\end{array}$ (9) | 0.1<br>0.01 | 98<br>60 |
| $\begin{array}{c}CH_3O\\ \phantom{xx}\diagdown\phantom{x}\underset{\|}{\overset{O}{P}}-N=CH-N(C_2H_5)_2\\ CH\equiv C-CH_2S\phantom{xx}\diagup\end{array}$ (3) | 0.1<br>0.01 | 100<br>98 |
| $\begin{array}{c}C_2H_5O\\ \phantom{xx}\diagdown\phantom{x}\underset{\|}{\overset{O}{P}}-N=CH-N(C_2H_5)_2\\ CH\equiv C-CH_2S\phantom{xx}\diagup\end{array}$ (7) | 0.1 | 100 |
| $\begin{array}{c}C_2H_5O\\ \phantom{xx}\diagdown\phantom{x}\underset{\|}{\overset{O}{P}}-N=CH-N(C_2H_5)_2\\ CH_3-CH=CH-CH_2S\phantom{xx}\diagup\end{array}$ (6) | 0.1 | 100 |

Table 4-continued

| Active compound (Tetranychus test/resistant) | Active compound concentration in % by weight | Degree of destruction in % after 2 days |
|---|---|---|
| $\begin{array}{c}C_2H_5O\\ \diagdown \\ \quad\quad P-N=CH-N(C_2H_5)_2\\ \diagup \\ CH_3-NH-CO-CH_2S\end{array}$ (5) | 0.1<br>0.01 | 100<br>60 |
| $\begin{array}{c}CH_3O\\ \diagdown \\ \quad\quad P-N=CH-N(C_3H_7)_2\\ \diagup \\ CH_3S\end{array}$ (12) | 0.1 | 99 |
| $\begin{array}{c}CH_3O\\ \diagdown \\ \quad\quad P-N=CH-N(CH_2-CH=CH_2)_2\\ \diagup \\ CH_3S\end{array}$ (13) | 0.1 | 100 |
| $\begin{array}{c}CH_3O\\ \diagdown \\ \quad\quad P-N=CH-N\bigcirc\\ \diagup \\ CH_3S\end{array}$ (19) | 0.1 | 99 |
| $\begin{array}{c}CH_3O\quad S\\ \diagdown \\ \quad\quad P-N=CH-N\bigcirc O\\ \diagup \\ CH_3S\end{array}$ (15) | 0.1 | 100 |
| $\begin{array}{c}CH_3O\\ \diagdown \\ \quad\quad P-N=CH-N\bigcirc O\\ \diagup \\ CH_3S\end{array}$ (16) | 0.1 | 98 |

EXAMPLE 5

Myzus test (systemic long-term action)

Solvet: 3 parts by weight of acetone
Emulsifier: 1 part by weight of alkylaryl polyglycol ether To produce a suitable prepartion of active compound, 1 part by weight of the active compond was mixed with the indicated amount of solvent which contained the indicated amount of emulsifier, and the concentrate was diluted with water to the desired concentration of 0.025% of active compound.

Cabbage plants (Brassica oleracea) were watered, each with 50 ml of the preparation of the active compound, so that the preparation of the active compound penetrated into the soil without wetting the leaves of the cabbage plants. The active compound was absorbed by the cabbage plants from the soil and thus reached the leaves. 12.5 mg of active compound were used per 100 g of soil (weighed air-dry).

After the indicated periods of time, the plants were infested with aphids (Myzus persicae) and their mortality was in each case determined after 3 days. Here, 100% means that all aphids were killed and 0% means that no aphids were killed.

The active compounds, the concentration of the active compounds, the evaluation times and the results can be seen from the following Table 5:

Table 5

| Active compound | Long-term action after watering: (Myzus persicae/Brassica oleracea) | | | | | | | |
|---|---|---|---|---|---|---|---|---|
| | mg of active compound per 100 g of soil (weighed air-dry) | % destruction after (days) | | | | | | |
| | | 20 | 27 | 34 | 41 | 45 | 48 | 52 |
| $\begin{array}{c}CH_3S\\ \diagdown \\ \quad\quad P-NH-CO-CH_3\\ \diagup \\ C_2H_5O\end{array}$ (known) (B) | 12.5 | 100 | 90 | 50 | 0 | | | |

Table 5-continued

| Active compound | Long-term action after watering: (Myzus persicae/Brassica oleracea) mg of active compound per 100 g of soil (weighed air-dry) | % destruction after (days) | | | | | |
|---|---|---|---|---|---|---|---|
| | | 20 | 27 | 34 | 41 | 45 | 48 | 52 |
| 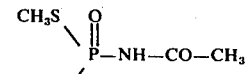 CH₃S\\ O‖ /P—NH—CO—CH₃ CH₃O  (known) (A) | 12.5 | 100 | 100 | 100 | 100 | 80 | 0 | 0 |
| 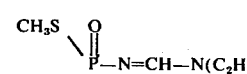 CH₃S\\ O‖ /P—N=CH—N(C₂H₅)₂ CH₃O  (1) | 12.5 | 100 | 100 | 100 | 100 | 100 | 100 | 100 |
| 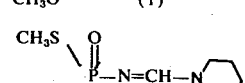 CH₃S\\ O‖ /P—N=CH—N◯ CH₃O (19) | 12.5 | 100 | 100 | 100 | 100 | 100 | 100 | 100 |
| 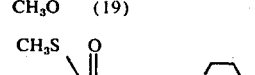 CH₃S\\ O‖ /P—N=CH—N◯O CH₃O (16) | 12.5 | 100 | 100 | 100 | 100 | 100 | 100 | 100 |

EXAMPLE 6

Tetranychus test (systemic long-term action)

Solvent: 3 parts by weight of acetone

Emulsifier: 1 part by weight of alkylaryl polyglycol ether

To produce a suitable preparation of active compound, 1 part by weight of the active compound was mixed with the indicated amount of solvent containing the indicated amount of emulsifier and the concentrate thus obtained was diluted with water to the desired concentration of 0.025% of active compound.

Bean plants (*Phaseolus vulgaris*) were watered, each with 50 ml of the preparation of the active compound, so that the preparation of the active compound penetrated into the soil without wetting the leaves of the plants. The active compound was absorbed by the plants from the soil and thus reached the leaves. 12.5 mg of active compound were used per 100 g of soil (weighed air-dry).

After the indicated periods of time, the plants wee infested with spider mites (*Tetranychus urticae*) and their mortality was in each case determined after 3 days. Here, 100% means that all spider mites were killed and 0% means that no spider mites were killed.

The active compounds, the concentration of the active compounds, the evaluation times and the results can be seen from the following Table 6:

Table 6

| Active compound | Long-term action after watering: (Tetranychus urticae (resistant)/Phaseolus vulgaris) mg of active compound per 100 g of soil (weighed air-dry) | % destruction after (days) | | | | | |
|---|---|---|---|---|---|---|---|
| | | 6 | 10 | 13 | 17 | 24 | 27 |
| 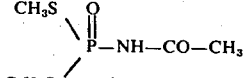 CH₃S\\ O‖ /P—NH—CO—CH₃ C₂H₅O  (known) (B) | 12.5 | 35 | 35 | 0 | | | |
| 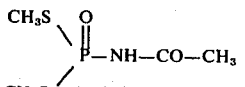 CH₃S\\ O‖ /P—NH—CO—CH₃ CH₃O  (known) (A) | 12.5 | 95 | 95 | 95 | 83 | 0 | |
| 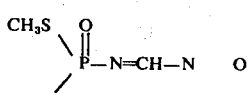 CH₃S\\ O‖ /P—N=CH—N   O CH₃O (16) | 12.5 | 100 | 100 | 100 | 100 | 100 | 100 |
| 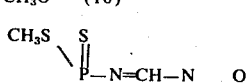 CH₃S\\ S‖ /P—N=CH—N   O CH₃O (15) | 12.5 | 100 | 100 | 100 | 100 | 100 | — |

The following examples illustrate the synthesis of the compounds.

EXAMPLE 7 a)  $(C_2H_5)_2N-CH\begin{smallmatrix}OCH_3\\OCH_3\end{smallmatrix}$

790 G (7.8moles) of N,N-diethylformamide were treated with 985 g of dimethyl sulfate while stirring, in the course of which the temperature of the mixture rose to 40°C. After stirring overnight, the reaction mixture was allowed to run into 7.8 mols of sodium methylate in methanol (total volume approximately 2.3 liters) at 0° to 5°C, while stirring, and the batch was again stirred overnight. Thereafer the methanol was first distilled from the crystal paste, following which the desired product was distilled off at 10 mm Hg up to a bath temperature of 17°C and was fractionated through a column. 862 g (75% of theory) of N,N-diethylformamide-dimethylacetal of boiling point 70°C/50 mm Hg (with foaming) and refractive index $n_D^{24} = 1.4074$ were obtained.

The following compounds were prepared analogously:

| Formula | Physical properties |
|---|---|
| $(nC_3H_7)_2N-CH\begin{smallmatrix}OCH_3\\OCH_3\end{smallmatrix}$ | Boiling point 44°C/ 2 mm Hg |
| $(nC_4H_9)_2N-CH\begin{smallmatrix}OCH_3\\OCH_3\end{smallmatrix}$ | Boiling point 74–75°C/12 mm Hg $n_D^{20}=1.4248$ |
| $(iC_4H_9)_2N-CH\begin{smallmatrix}OCH_3\\OCH_3\end{smallmatrix}$ | Boiling point 62°C/ 1 mm Hg |
| pyrrolidinyl-CH(OCH_3)_2 | Boiling point 160–161°C/740 mm Hg $n_D^{20}=1.4230$ |
| piperidinyl-CH(OCH_3)_2 | Boiling point 83°C/ 15 mm Hg $n_D^{20}=1.4411$ |
| morpholinyl-CH(OCH_3)_2 | Boiling point 87°C/ 15 mm Hg $n_D^{20}=1.4811$ |
| $(CH_2=CH-CH_2)_2N-CH\begin{smallmatrix}OCH_3\\OCH_3\end{smallmatrix}$ | Boiling point 50°C/ 2 mm Hg | b) $\begin{smallmatrix}CH_3O\\CH_3S\end{smallmatrix}>\!\!\!\underset{\|}{\overset{O}{P}}\!-\!N\!=\!CH\!-\!N(C_2H_5)_2$  (1)

A mixture of 42 g (0.3 mole) of O,S-dimethylthiolphosphoric acid ester amide and 55 g (0.46 mole) of N,N-diethylformamide-dimethylacetal was warmed to 120°C for 5 hours and subsequently subjected to slight distillation. 62.5 g (93% of theory) of O,S-dimethyl-N-(N',N'-diethylaminomethylidene)-thiolphosphoric acid ester imide of refractive index $n_D^{24} = 1.5218$ were obtained.

EXAMPLE 8 a) $\begin{smallmatrix}CH_3O\\CH_3S\end{smallmatrix}>\!\!\!\underset{\|}{\overset{O}{P}}\!-\!N\!=\!CH\!-\!OC_2H_5$ A mixture of 71 g (0.5 mol) of O,S-dimethyl-thiolphosphoric acid ester amide and 92 g of orthoformic acid ethyl ester was boiled for 4 hours under reflux and the ethanol formed was subsequently distilled off. After slight distillation of the residue, 56 g (57% of theory of the desired N-(O,S-dimethylthiolphosphoryl)-iminoformic acid ethyl ester of boiling point 84°C/0.01 mm Hg and refractive index $n_D^{22} = 1.4892$ were obtained.

The following compound was prepared analogously:

$\begin{smallmatrix}CH_3S\\C_2H_5O\end{smallmatrix}>\!\!\!\underset{\|}{\overset{O}{P}}\!-\!N\!=\!CH\!-\!OC_2H_5$  $n_D^{27} = 1.4802$ Boiling point 88°C/0.01 mm Hg b) $\begin{smallmatrix}C_2H_5O\\C_2H_5S\end{smallmatrix}>\!\!\!\underset{\|}{\overset{O}{P}}\!-\!N\!=\!CH\!-\!N(C_2H_5)_2$  (2)

A mixture of 40 g (0.2 mole) of N-(O,S-diethylthiolphosphoryl)-iminoformic acid ethyl ester and 15 g (0.2 mole) of diethylamine was stirred for 2 hours at 40°C and subsequently subjected to "slight distillation". 40 g (89% of theory) of O,S-diethyl-N-(N',N'-diethylaminomethylidene)-thiolphosphoric acid ester imide of refractive index $n_D^{25} = 1.5013$ were obtained.

The following compounds were prepared by methods analogous to those of Examples 7 and 8.

| Formula | Physical properties refractive index |
|---|---|
| (3) $CH_3-\overset{C-CH_2-S}{\underset{CH_3O}{\phantom{x}}}>\!\!\underset{\|}{\overset{O}{P}}\!-\!N\!=\!CH\!-\!N(C_2H_5)_2$ | $n_D^{22} = 1.5417$ |
| (4) $C_2H_5S-CH_2-CH_2-\overset{S}{\underset{C_2H_5O}{\phantom{x}}}>\!\!\underset{\|}{\overset{O}{P}}\!-\!N\!=\!CH\!-\!N(C_2H_5)_2$ | $n_D^{22} = 1.5308$ |
| (5) $CH_3-NH-CO-CH_2-\overset{S}{\underset{C_2H_5O}{\phantom{x}}}>\!\!\underset{\|}{\overset{O}{P}}\!-\!N\!=\!CH\!-\!N(C_2H_5)_2$ | $n_D^{24} = 1.5268$ |
| (6) $CH_3-CH=CH-CH_2-\overset{S}{\underset{C_2H_5O}{\phantom{x}}}>\!\!\underset{\|}{\overset{O}{P}}\!-\!N\!=\!CH\!-\!N(C_2H_5)_2$ | $n_D^{24} = 1.5133$ |
| (7) $CH_3-\overset{C-CH_2-S}{\underset{C_2H_5O}{\phantom{x}}}>\!\!\underset{\|}{\overset{O}{P}}\!-\!N\!=\!CH\!-\!N(C_2H_5)_2$ | $n_D^{22} = 1.5310$ |
| (8) $CH_2=CH-CH_2-\overset{S}{\underset{CH_3O}{\phantom{x}}}>\!\!\underset{\|}{\overset{O}{P}}\!-\!N\!=\!CH\!-\!N(C_2H_5)_2$ | $n_D^{24} = 1.5229$ |
| (9) $CH_2=CH-CH_2-\overset{S}{\underset{C_2H_5O}{\phantom{x}}}>\!\!\underset{\|}{\overset{O}{P}}\!-\!N\!=\!CH\!-\!N(C_2H_5)_2$ | $n_D^{24} = 1.5178$ |

-continued

| Formula | Physical properties refractive index) |
|---|---|
| (10) C₂H₅S\P(=O)(/CH₃O)—N=CH—N(C₂H₅)₂ | $n_D^{22} = 1.5139$ |
| (11) CH₃S\P(=S)(/CH₃O)—N=CH—N(C₂H₅)₂ | $n_D^{25} = 1.5148$ |
| (12) CH₃S\P(=O)(/CH₃O)—N=CH—N(C₃H₇)₂ | $n_D^{24} = 1.5052$ |
| (13) CH₃S\P(=O)(/CH₃O)—N=CH—N(CH₂—CH=CH₂)₂ | $n_D^{25} = 1.5331$ |
| (14) C₂H₅S\P(=O)(/C₂H₅O)—N=CH— 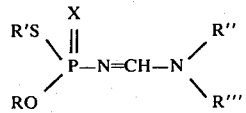 | $n_D^{22} = 1.5432$ |
| (15) CH₃S\P(=S)(/CH₃O)—N=CH—N(morpholino) | $n_D^{23} = 1.5804$ |
| (16) CH₃S\P(=O)(/CH₃O)—N=CH—N(morpholino) | $n_D^{23} = 1.5432$ |
| (17) CH₃S\P(=O)(/C₂H₅O)—N=CH—N(morpholino) | $n_D^{25} = 1.5428$ |
| (18) CH₃S\P(=O)(/CH₃O)—N=CH—N(C₄H₉i)₂ | $n_D^{25} = 1.4981$ |
| (19) CH₃S\P(=O)(/CH₃O)—N=CH—N(piperidino) | $n_D^{23} = 1.5480$ |
| (20) CH₃S\P(=O)(/CH₃O)—N=CH—N(pyrrolidino) | $n_D^{24} = 1.5523$ |
| (21) CH₃S\P(=O)(/C₂H₅O)—N=CH—N(C₂H₅)₂ | $n_D^{25} = 1.5131$ |

It will be appreciated that the instant specification and examples are set forth by way of illustration and not limitation, and that various modifications and changes may be made without departing from the spirit and scope of the present invention.

What is claimed is:

1. An N-(N',N'-distubstituted aminomethylidene)-(thiono)-thiol phosphoric acid ester imide of the formula $$\begin{array}{c} R'S \\ \diagdown \\ RO \end{array} P(=X) - N=CH - N \begin{array}{c} R'' \\ \diagup \\ R''' \end{array}$$

in which
R is alkyl with 1 to 6 carbon atoms.
R' is lower alkylmercapto-lower alkyl or N-alkylcarbamoylmethyl,
R'' and R''' each independently is ethyl, n-propyl, isopropyl, n-butyl, isobutyl, sec.-butyl, tert.-butyl, n-pentyl, n-hexyl or allyl, and
X is oxygen or sulfur.

2. A compound according to claim 1, in which R is lower alkyl, R' is N-mono-methylcarbamoylmethyl, N-monoethylcarbamoylmethyl, methylmercaptoethyl or ethylmercaptoethyl.

3. The compound according to claim 1, wherein such compound is O-ethyl-S-(ethylmercaptoethyl)-N-(N',N'-diethylaminomethylidene)-thiolphosphoric acid ester amide of the formula

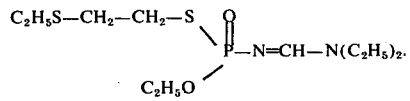

4. The compond according to claim 1, wherein such compound is O-ethyl-S-(N'-monomethylcarbamoylmethyl)-N-(N',N'-diethylaminomethylidene)-thiolphosphoric acid ester imide of the formula

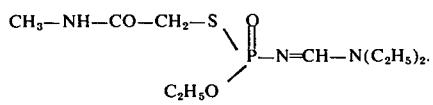

* * * * *